United States Patent [19]

Lang et al.

[11] Patent Number: 5,591,754

[45] Date of Patent: Jan. 7, 1997

[54] BENZOYLGUANIDINES, PHARMACEUTICAL COMPOSITION CONTAINING THEM AND TREATMENT OF ARRTHYTHMIAS THEREWITH

[75] Inventors: Hans-Jochen Lang, Hofheim/Taunus; Andreas Weichert, Frankfurt am Main; Heinz-Werner Kleemann, Bad Homburg; Heinrich Englert, Hofheim/Taunus; Wolfgang Scholz, Eschborn; Udo Albus, Florstadt, all of Germany

[73] Assignee: Hoechst Aktiengesellschaft, Frankfurt am Main, Germany

[21] Appl. No.: 437,552

[22] Filed: May 5, 1995

Related U.S. Application Data

[63] Continuation of Ser. No. 123,208, Sep. 20, 1993.

[30] Foreign Application Priority Data

Sep. 22, 1992 [DE] Germany .............. 42 31 658.8
Dec. 16, 1992 [DE] Germany .............. 42 42 587.5

[51] Int. Cl.$^6$ ............ A61K 31/165; A61K 31/445; C07C 317/48; C07D 211/28
[52] U.S. Cl. ............ 514/331; 514/603; 514/618; 540/231; 564/86; 564/162
[58] Field of Search .............. 546/231; 564/86, 564/162; 514/331, 603, 618

[56] References Cited

U.S. PATENT DOCUMENTS

| | | | |
|---|---|---|---|
| 3,780,027 | 12/1973 | Cragoe, Jr. et al. | 260/239.6 |
| 5,091,394 | 2/1992 | Englert et al. | 514/331 |
| 5,292,755 | 3/1994 | Englert et al. | 514/331 |

FOREIGN PATENT DOCUMENTS

0416499A3  3/1991  European Pat. Off. .

OTHER PUBLICATIONS

Schmid et al., "Na$^+$/H$^+$ Exchange In Porcine Cerebral Capillary Endothelial Cells Is Inhibited By a Benzoylguanidine Derivative", Biochem. and Biophys. Research Communications, 184(1):112–117 (1992).

*Primary Examiner*—Richard L. Raymond
*Attorney, Agent, or Firm*—Finnegan, Henderson, Farabow, Garrett & Dunner, L.L.P.

[57] ABSTRACT

Benzoylguanidines, process for their preparation, their use as a medicament and medicament containing them.

The invention relates to benzoylguanidines of the formula I

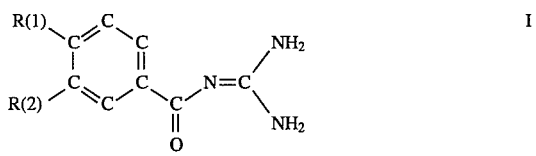

where R(1) or R(2) is R(3)-S(O)$_n$— or R(4)R(5)N—O$_2$S— and the other substituent R(1) or R(2) in each case is H, OH, F, Cl, Br, I, alkyl, alkoxy, benzyloxy or phenoxy, R(3)-S(O)$_n$ or R(4)R(5)N— or 3,4-dehydropiperidine and R(3) is alkyl, cycloalkyl, cyclopentylmethyl, cyclohexylmethyl or phenyl, R(4) and R(5) are alkyl or phenylalkyl or phenyl, and in which R (4) and R (5) can also together be a C$_4$–C$_7$-chain, and in which R(4) and R(5), together with the nitrogen atom to which they are bonded, can be a dihydroindole, tetrahydroquinoline or tetrahydroisoquinoline system,
and where n is zero, 1 or 2 and their pharmaceutically tolerable salts are excellent antiarrhythmics.

5 Claims, No Drawings

BENZOYLGUANIDINES, PHARMACEUTICAL COMPOSITION CONTAINING THEM AND TREATMENT OF ARRTHYTHMIAS THEREWITH

This application is a continuation of application Ser. No. 08/123,208 filed Sep. 20, 1993, now abandoned.

DESCRIPTION

Benzoylguanidines, process for their preparation, their use as a medicament and medicament containing them The invention relates to benzoylguanidines of the formula I

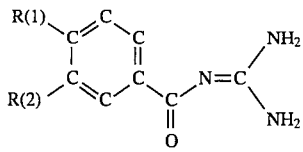

in which:
R (1) or R (2) is
R(3)-S(O)n— or

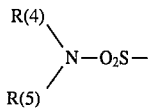

the other substituent R(1) or R(2) in each case is
H, OH, F, Cl, Br, I, $C_1$-$C_4$-alkyl, $C_1$-$C_4$-alkoxy, benzyloxy or phenoxy, which is unsubstituted or carries one to three substituents from the groups fluorine, chlorine, methyl, methoxy, hydroxyl or benzyloxy,
R(3)-S(O)$_n$ or

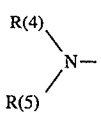

or 3,4-dehydropiperidine
R(3) is $C_1$-$C_6$-alkyl, $C_5$-$C_7$-cycloalkyl, cyclopentylmethyl, cyclohexylmethyl or phenyl, which is unsubstituted or carries one to three substituents from the groups fluorine, chlorine, methyl or methoxy,
R(4) and R(5)—identical or different—are H, $C_1$-$C_6$-alkyl or
R(4) is phenyl — $(CH_2)_m$—
where m is 1, 2, 3 or 4, phenyl,
which is unsubstituted or carries one or two substituents from the groups fluorine, chlorine, methyl or methoxy,
R(4) and R(5) can also together be a straight-chain or branched $C_4$-$C_7$-chain, where the chain can additionally be interrupted by O, S or NR(6),
R(6) is H or methyl,
or
R(4) and R(5), together with the nitrogen atom to which they are bonded, can be a dihydroindol, tetrahydroquinoline or tetrahydroisoquinoline system,
n is zero, 1 or 2,
and their pharmaceutically tolerable salts.

If the substituents R(1) and R(2) contain one or more centers of asymmetry, the invention includes compounds having both the S and R configuration. The compounds can be present as optical isomers, as diastereomers, as racemates or as mixtures thereof. The alkyl radicals designated can be straight-chain or branched.

Preferred compounds of the formula I are those in which:
R(1) is $C_1$-$C_4$-alkyl, phenoxy or phenyl-NH—, in which phenyl is unsubstituted or carries one to three substituents from the groups fluorine, chlorine or methyl,
R(2) is methylsulfonyl,
and their pharmacologically tolerable salts.

The compounds 4-ethylamino-3-methylsulfonylbenzoylguanidine hydrochloride, 4-N,N-diethylamino-3-methylsulfonylbenzoylguanidine hydrochloride, 4-(4-chlorophenoxy)-3-methylsulfonylbenzoylguanidine hydrochloride, 4-(3-chloro-4-fluorophenoxy)-3-methylsulfonylbenzoylguanidine hydrochloride, 4-(4-fluorophenoxy)-3-methylsulfonylbenzoylguanidine hydrochloride, 4-(4-fluoroanilino)-3-methylsulfonylbenzoylguanidine hydrochloride, 4-(3-chloro-4-fluoroanilino)-3-methylsulfonylbenzoylguanidine hydrochloride, 4-isopropyl-3-sulfonylbenzoylguanidine hydrochloride, 4-isopropyl-3-methylsulfonylbenzoylguanidine methanesulfonate, 4-phenoxy-3-methylsulfonylbenzoylguanidine hydrochloride, 3-methylsulfonyl-4-(2,6-cis-dimethylpiperidino)benzoylguanidine methanesulfonate, 4-(1-methylpropyl)-3-methylsulfonylbenzoylguanidine hydrochloride, 4-butyl-3-methylsulfonylbenzoylguanidine hydrochloride, 4-(2-methylpropyl)-3-methylsulfonylbenzoylguanidine hydrochloride, 4-(4-hydroxyphenoxy)3-methylsulfonylbenzoylguanidine hydrochloride are particularly preferred.

The compounds 4-isopropyl-3-methylsulfonylbenzoylguanidine methanesulfonate, 4-isopropyl-3-methylsulfonylbenzoylguanidine hydrochloride, 4-phenoxy-3-methylsulfonylbenzoylguanidine hydrochloride, 4-(4-chlorophenoxy)-3-methylsulfonylbenzoylguanidine hydrochloride and their other pharmacologically tolerable salts are very particularly preferred.

The compound 4-isopropyl-3-methylsulfonylbenzoylguanidine methanesulfonate is particularly preferred.

The compounds I are substituted acylguanidines. The most prominent representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

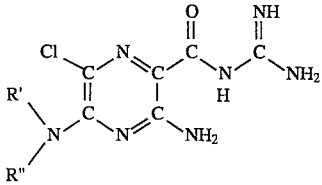

Amiloride: R', R''=H
Dimethylamiloride: R', R''=$CH_3$
Ethyl isopropylamiloride: R'=$C_2H_5$, R''=$CH(CH_3)$ Investigations have moreover been disclosed which point to antiarrhythmic properties of amiloride [Circulation 79; 1257–63 (1989)]. Obstacles to wide use as an antiarrhythmic are, however, that this effect is only slightly pronounced and occurs accompanied by a hypotensive and saluretic action and these side effects are undesired in the treatment of cardiac arrhythmias.

Indications of antiarrhythmic properties of amiloride were also obtained in experiments on isolated animal hearts (Eur. Heart J. 9 (suppl.1):167 (1988) (book of abstracts)). For instance, it was found in rat hearts that an artificially induced ventricular fibrillation could be suppressed completely by amiloride. The above-mentioned amiloride derivative ethylisopropylamiloride was even more potent than amiloride in this model.

Benzoylguanidines having antiarrhthymic properties are described in European Offenlegungsschrift 416 499.

In U.S. Pat. No. 3,780,027, acylguanidines are described which are structurally similar to the compounds of the formula I. The crucial difference to the compounds I is that they are trisubstituted benzoylguanidines which in their substitution pattern are derived from commercially available diuretics, such as bumetanide and furosemide, and carry an amino group in position 2 or 3 relative to the carbonylguanidine group which is important for the salidiuretic action desired. A strong salidiuretic activity is correspondingly reported for these compounds.

It was therefore surprising that the compounds according to the invention have no undesired and disadvantageous salidiuretic properties, but very good antiarrhythmic properties, as occur, for example, in the case of oxygen deficiency symptoms. As a result of their pharmacological properties, the compounds are outstandingly suitable as antiarrhythmic pharmaceuticals having a cardioprotective component for infarct prophylaxis and infarct treatment and for the treatment of angina pectoris, where they also preventively prohibit or greatly decrease the pathophysiological processes in the formation of ischemically induced damage, in particular in the production of ischemically induced cardiac arrhythmias. Because of their protective actions against pathological hypoxic and ischemic situations, the compounds of the formula I according to the invention can be used as a result of inhibition of the cellular $Na^+/H^+$ exchange mechanism as pharmaceuticals for the treatment of all acute or chronic damage caused by ischemia or primary or secondary diseases induced thereby. This relates to their use as pharmaceuticals for surgical interventions, for example in organ transplantation, where the compounds can be used both for the protection of the organs in the donor before and during removal, for the protection of removed organs, for example during treatment with or storage thereof in physiological bath fluids, and during transfer to the body of the recipient. The compounds are also useful protective pharmaceuticals during the performance of angioplastic surgical interventions, for example in the heart and in peripheral vessels. In accordance with their protective action against ischemically induced damage, the compounds are also suitable as pharmaceuticals for the treatment of ischemias of the nervous system, in particular the CNS, where they are suitable, for example, for the treatment of stroke or of cerebral edema.

Moreover, the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I can therefore be considered as useful therapeutics for diseases in which cell proliferation is a primary or secondary cause, and can therefore be used as antiatherosclerotics, agents against diabetic late complications, cancers, fibrotic diseases such as pulmonary fibrosis, fibrosis of the liver or fibrosis of the kidneys, organ hypertrophy and hyperplasia, in particular in prostate hyperplasia or prostate hypertrophy.

The compounds according to the invention are active inhibitors of the cellular sodium-proton antiporter ($Na^+/H^+$ exchanger), which is raised in numerous diseases (essential hypertension, atherosclerosis, diabetes, etc.) even in those cells which are easily accessible to measurements, such as, for example, in erythrocytes, thrombocytes or leucocytes. The compounds according to the invention are therefore suitable as excellent and simple scientific tools, for example in their use as diagnostics for the determination and differentiation of certain forms of hypertension, but also of atherosclerosis, of diabetes, proliferative diseases etc. Moreover, the compounds of the formula I are suitable for preventive therapy for the prevention of the formation of high blood pressure, for example of essential hypertension.

The invention furthermore relates to a process for the preparation of the compounds I, which comprises reacting compounds of the formula II

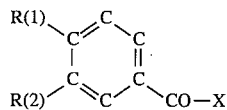

in which R(1) and R(2) have the given meaning and X is a leaving group which can be easily substituted nucleophilically with guanidine.

The activated acid derivatives of the formula II in which X is an alkoxy group, preferably a methoxy group, a phenoxy group, a phenylthio, methylthio or 2-pyridylthio group, or a nitrogen heterocycle, preferably 1-imidazolyl, are advantageously obtained in a manner known per se from the carbonyl chlorides (formula II, X=Cl) on which they are based, which for their part can in turn be prepared in a manner known per se from the carboxylic acids (formula II, X=OH) on which they are based, for example using thionyl chloride.

In addition to the carbonyl chlorides of the formula II (X=Cl), other activated acid derivatives of the formula II can also be prepared in a manner known per se directly from the benzoic acid derivatives (formula II, X=OH) on which they are based, such as, for example, the methyl esters of the formula II where $X=OCH_3$ by treatment with gaseous HCl in methanol, the imidazolides of the formula II by treatment with carbonyldiimidazole (X=1-imidazolyl, Staab, Angew. Chem. Int. Ed. Engl. 1, 351–367 (1962)), the mixed anhydrides II using $Cl-COOC_2H_5$ or tosyl chloride in the presence of triethylamine in an inert solvent, and also the activation of benzoic acids using dicyclohexylcarbodiimide (DCC). A number of suitable methods for the preparation of activated carboxylic acid derivatives of the formula II are given under details of source literature in J. March, Advanced Organic Chemistry, Third Edition (John Wiley & Sons, 1985), p. 350.

The reaction of an activated carboxylic acid derivative of the formula I with guanidine is carried out in a manner known per se in a protic or aprotic polar but inert organic solvent. Methanol or THF between 20° C. and the boiling point of these solvents have proven suitable in the reaction of the methyl benzoates (II, X=OMe) with guanidine. In most reactions of compounds II with guanidine, the reaction was advantageously carried out in aprotic inert solvents such as THF, dimethoxyethane or dioxane. However, water can also be used as a solvent in the reaction of II and guanidine.

If X=Cl, the reaction is advantageously carried out with the addition of an acid scavenger, for example in the form of excess guanidine for binding the hydrohalic acid.

Some of the underlying benzoic acid derivatives of the formula II are known and described in the literature. The unknown compounds of the formula II can be prepared by methods known from the literature by converting, for example, 4-chloro- or 4-fluoro-3-chlorosulfonylbenzoic acid with ammonia or an amine into a 3-aminosulfonyl-4-chloro- or fluorobenzoic acid (IIIa) or with a weak reductant such as sodium bisulfite and subsequent alkylation to a 3-alkylsulfonyl-4-chloro or -4-fluorobenzoic acid (IIIb, n=2)

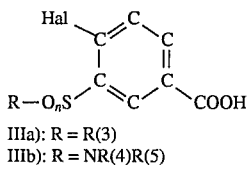

IIIa): R = R(3)
IIIb): R = NR(4)R(5)

and reacting the benzoic acids obtained by one of the process variants described above to give compounds I according to the invention.

Compounds of the formulae IIIa) and b) can also be used, however, as starting compounds for other carboxylic acids, it being possible to replace the halogen in the R(1) position very conveniently by numerous nucleophilic reagents, such as mercaptans R(3)-SH or primary amines R(4)R(5)NH with the formation of further benzoic acid derivatives II where X=OH. In a similar manner, starting from 3-nitro-4-chlorobenzoic acid, further benzoic acid derivatives (II, X=OH) can be prepared by nucleophilic introduction of a radical R(1) according to the invention in position 4 (replacement by Cl) and further modification of the nitro group, such as reduction to $NH_2$ and subsequent alkylation or displacement, for example by diazotization and sandmeyer reaction.

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates and p-toluenesulfonates.

Pharmaceuticals which contain a compound I can be administered orally, parenterally, intravenously, rectally or by inhalation, the preferred administration being dependent on the particular type of the disease. The compounds I can be used on their own or together with pharmaceutical auxiliaries, to be precise in veterinary and in human medicine. The auxiliaries which are suitable for the desired pharmaceutical formulation are familiar to the person skilled in the art on the basis of his expert knowledge. In addition to solvents, gelling agents, suppository bases, tabletting auxiliaries and other active compound excipients, antioxidants, dispersants, emulsifiers, antifoams, flavor correctants, preservatives, solubilizers or colorants, for example, can be used.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular cornstarch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example: water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents. If required, the formulation can also contain still other pharmaceutical auxiliaries such as surfactants, emulsifiers and stabilizers as well as a propellant gas. Such a preparation contains the active compound customarily in a concentration from about 0.1 to 10, in particular from about 0.3 to 3 % by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated.

On average, the daily dose of a compound of the formula I in a patient of weight about 75 kg is at least 0.001 mg, preferably 0.01 mg to at most 10 mg, preferably at most 1 mg. In acute episodes of the disease, for example immediately after suffering a cardiac infarct, even higher and in particular more frequent dosages may be necessary, for example up to 4 individual doses per day. In particular when administered i.v., for example in the case of an infarct patient in the intensive care unit up to 100 mg per day may be necessary.

EXAMPLES

General Procedure I for the Preparation of Benzoylguanidines (I) from Benzoic Acids (II, X=OH)

0.01 mol of the benzoic acid derivative of the formula II is dissolved or suspended in 60 ml of anhydrous tetrahydrofuran (THF) and then treated with 1.78 g (0.011 mol) of carbonyldiimidazole. After stirring for 2 hours at room temperature, 2.95 g (0.05 mol) of guanidine is introduced into the reaction solution. After stirring overnight, the THF is distilled off under reduced pressure (rotary evaporator), the residue is treated with water, the mixture is adjusted to pH 6–7 using 2N HCL and the corresponding benzoylguanidine (formula I) is filtered off. The benzoylguanidines thus obtained can be converted into the corresponding salts by treatment with aqueous or methanolic hydrochloric acid or other pharmacologically tolerable acids.

General procedure II for the preparation of benzoylguanidines (I) from benzoic acid esters (general formula II, X=alkoxy or phenoxy) 1 equivalent of an appropriate benzoic acid ester of the formula II and 5.0 equivalents of guanidine are dissolved in isopropanol or suspended in THF, and the mixture is then boiled under a reflux condenser (reaction time about 2–5 hours) until reaction is complete (TLC checking). The solvent is distilled off under reduced pressure (in a rotary evaporator), the residue is taken up in ethyl acetate and the mixture is washed 3 times with saturated sodium hydrogen carbonate solution. Drying of the organic phase over sodium sulfate, removal of the solvent by distillation under reduced pressure and chromatography of the residue on silica gel using a suitable solvent. Conversion of the corresponding benzoylguanidine of the formula I obtained into the corresponding hydrochloride is carried out analogously to procedure 1.

EXAMPLE 1:

3-Methylsulfonyl-4-(1-pentylamino)benzoylguanidine hydrochloride, m.p.: 162°–165° C.

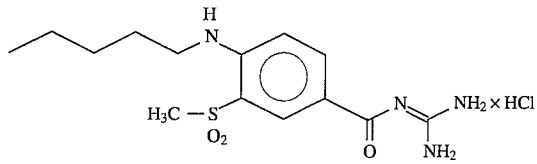

EXAMPLE 2:

3-Methylsulfonyl-4-(1,1-dipropylamino)benzoylguanidine hydrochloride, m.p.: 82°–84° C.

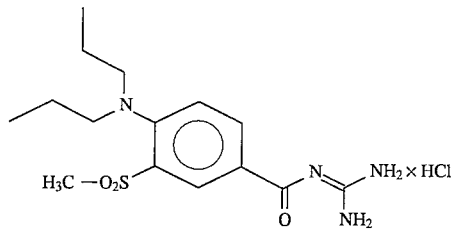

EXAMPLE 3:

3-Methylsulfonyl-4-(1-propylamino)benzoylguanidine hydrochloride, m.p.: 170°–174° C.

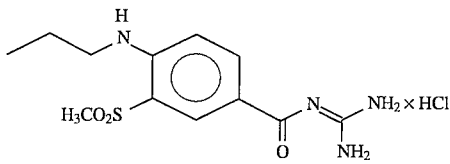

EXAMPLE 4:

3-Methylsulfonyl-4-(N-thiomorpholino)benzoylguanidine hydrochloride, m.p.: 264° C.

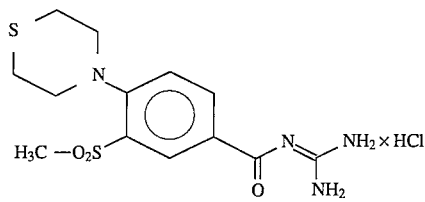

EXAMPLE 5:

4-Methylamino-3-methylsulfonylbenzoylguanidine hydrochloride, m.p.: 266° C.

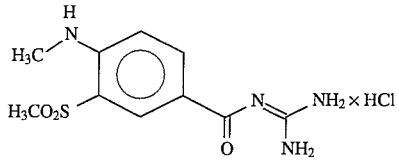

EXAMPLE 6:

4-Chloro-3-cyclopentylsulfonylbenzoylguanidine hydrochloride, m.p.: 205°–208° C.

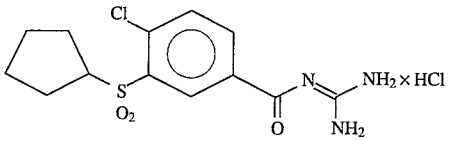

EXAMPLE 7:

4-Chloro-3-(2,5-dimethoxy-4-methylphenylsulfonyl)benzoylguanidine hydrochloride, m.p.: 248° C.

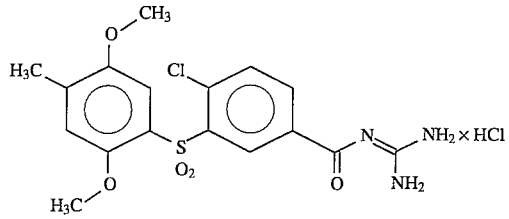

EXAMPLE 8:

4-(3,4-Dehydropiperidino)-3-methylsulfonylbenzoyl guanidine hydrochloride, m.p.: 207° C.

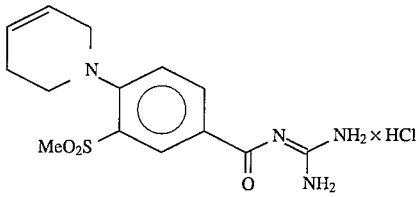

EXAMPLE 9:

4-Ethylamino-3-methylsulfonylbenzoylguanidine hydrochloride, m.p.: 242° C.

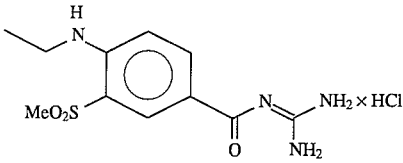

EXAMPLE 10:

4,N,N-Diethylamino-3-methylsulfonylbenzoylguanidine hydrochloride, m.p.: 274° C.

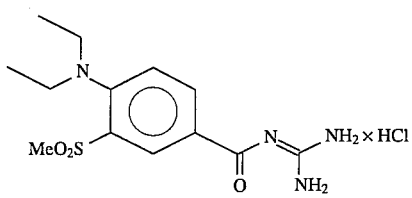

EXAMPLE 11:

4,N,N-Dimethylamino-3-methylsulfonylbenzoylguanidine dihydrochloride, m.p.: 177° C.

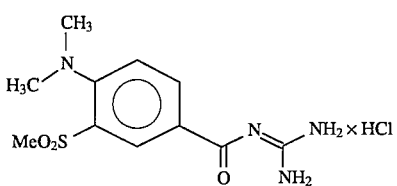

EXAMPLE 12:

4-(1-Butylamino)-3-methylsulfonylbenzoylguanidine hydrochloride, m.p.: 188° C.

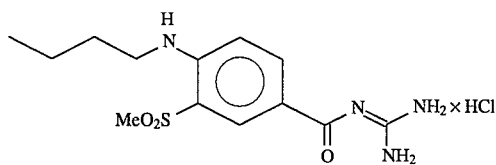

EXAMPLE 13:

4-(4-Chlorophenoxy)-3-methylsulfonylbenzoylguanidine hydrochloride, m.p.: 292°–293° C.

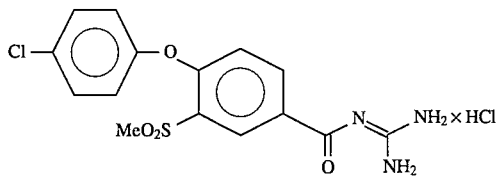

EXAMPLE 14:

4-(4-Chloro-3-methylphenoxy)-3-methylsulfonylbenzoylguanidine hydrochloride, m.p.: 290°–291° C.

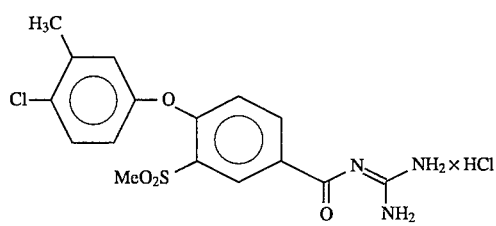

EXAMPLE 15:

4-(4-Chloro-3,5-dimethylphenoxy)-3-methylsulfonylbenzoylguanidine hydrochloride, m.p.: 273°–274° C.

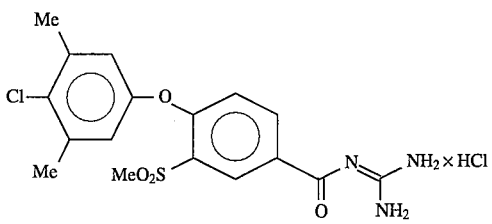

EXAMPLE 16:

4-(3-Chlorophenoxy)-3-methylsulfonylbenzoylguanidine hydrochloride, m.p.: 280° C.

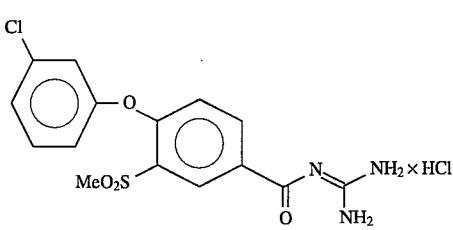

EXAMPLE 17:

4-(3-Chloro-4-fluorophenoxy)3-methylsulfonylbenzoylguanidine hydrochloride, m.p.: 284°–286° C.

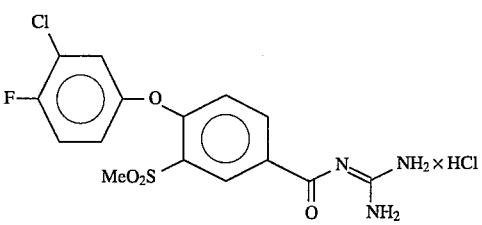

EXAMPLE 18:

4-(4-Fluorophenoxy)-3-methylsulfonylbenzoylguanidine hydrochloride, m.p.: 302°–304° C.

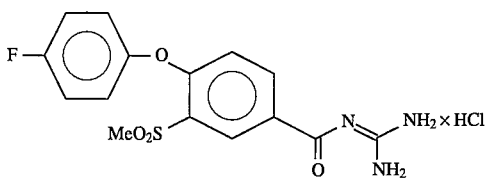

EXAMPLE 19:

4-(4-Fluoroanilino)-3-methylsulfonylbenzoylguanidine hydrochloride, m.p.: 287° C.

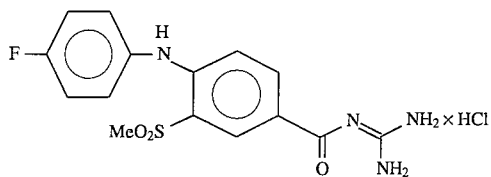

EXAMPLE 20:

4-(3-Chloro-4-fluoroanilino)-3-methylsulfonylbenzoylguanidine hydrochloride, m.p.: 298°–300° C.

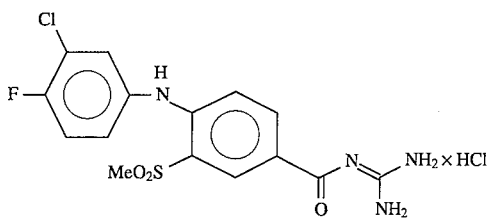

EXAMPLE 21:

4-Ethyl-3-methylsulfonylbenzoylguanidine hydrochloride, m.p.: 234°–237° C.

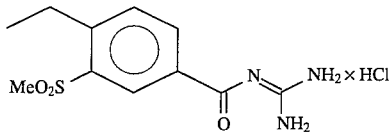

EXAMPLE 22:

4-Isopropyl-3-methylsulfonylbenzoylguanidine hydrochloride, m.p.: 268° C. (dec.).

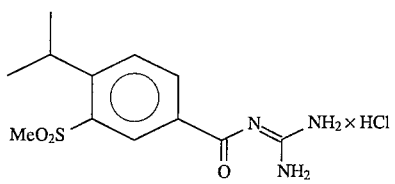

EXAMPLE 23:

4-Bromo-3-methylsulfonylbenzoylguanidine hydrochloride, m.p.: 250°–252° C.

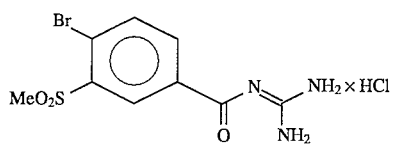

Synthesis route:
a) Reduction of 4-bromo-3-chlorosulfonylbenzoic acid to 2-bromo-5-carboxybenzenesulfinic acid using sodium disulfite in water at 10°–15° C. and constant pH (8–9), adjust to pH 1 using HCl and filter off the precipitate. Colorless crystals, m.p. 220° C.

b) Disodium 2-bromo-5-carboxybenzenesulfinate (m.p. >300° C.) is obtained from a) by treatment with 2 equivalents of NaOH in water/methanol, evaporating, suspending the residue in acetone and filtering off the crystals.

c) Methyl 4-bromo-3-methylsulfonylbenzoate (m.p. 148°–149° C.) is obtained from b) using 3.5 equivalents of methyliodide in DMF at 80° C. for 6 hours, distilling off the solvent, suspending the residue in water and filtering off the crystals.

d) 4-Bromo-3-methylsulfonylbenzoylguanidine hydrochloride is obtained from c) by boiling with guanidine in THF under a reflux condenser analogously to general procedure II and then treating with HCl to form the hydrochloride.

EXAMPLE 24:

4-Isopropyl-3-sulfamoylbenzoylguanidine hydrochloride, m.p.: 260° C.

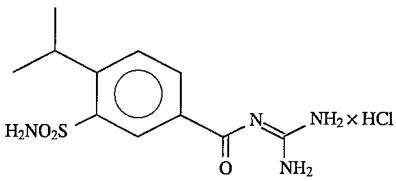

EXAMPLE 25:

4-Phenylsulfinyl-3-methylsulfonylbenzoylguanidine hydrochloride, m.p.: 209° C.

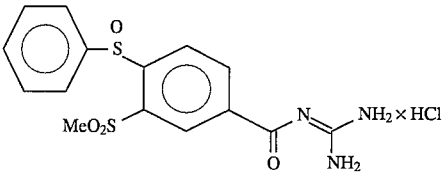

EXAMPLE 26:

4-Phenylsulfonyl-3-methylsulfonylbenzoylguanidine hydrochloride, m.p.: 258° C. (dec.).

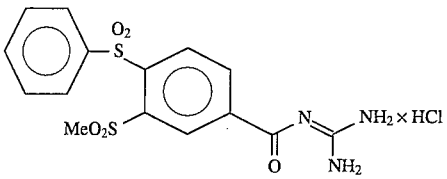

EXAMPLE 27:

4-Methyl-3-methylsulfonylbenzoylguanidine hydrochloride, m.p.: 236°–237° C.

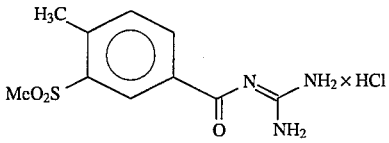

EXAMPLE 28:

4-(2-Chlorophenoxy)-3-methylsulfonylbenzoylguanidine hydrochloride, m.p.: 253–°255° C.

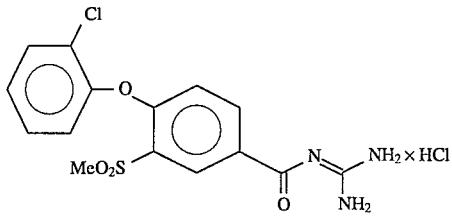

EXAMPLE 29:

4-Isopropyl-3-methylsulfonylbenzoylguanidine methanesulfonate, m.p.: 226°–228° C.
Synthesis route:
a)
4-Isopropyl-3-chlorosulfonylbenzoic acid (m.p. 203°–204 C.) by heating 4-isopropylbenzoic acid with chlorosulfonic acid at 95° C. for 3 hours
b)
2-Isopropyl-5-carboxybenzenesulfinic acid (m.p. 205°–207 C.) from a) by reduction with sodium sulfite at 60° C. in aqueous NaOH, at pH 9–10.
c)
4-Isopropyl-3-methylsulfonylbenzoic acid (m.p. 209°–211° C.) from b) by alkylation with methyl bromide in the presence of NaOH in DMF at 60° C. for 3 hours.
d)
4-Isopropyl-3-methylsulfonylbenzoylguanidine methanesulfonate from c) by reaction with thionyl chloride in toluene (reflux) for 1 hour. After evaporating the solvent, the residue is dissolved in THF and the solution is added to a mixture of guanidine hydrochloride, 2N NaOH and THF. After 4 hours at 30–40° C., the THF is removed by distillation and the crystalline 4-isopropyl-3-methylsulfonylbenzoylguanidine is filtered off. Reaction with methanesulfonic acid follows to form the salt.

EXAMPLE 30

3-Sulfamoylbenzoylguanidine hydrochloride, m.p.: 230° C.;

EXAMPLE 31

3-N,N-Diethylsulfamoylbenzoylguanidine hydrochloride, m.p.: 218° C.;

EXAMPLE 32

3-N-Cyclopentylsulfamoyl-4-piperidinobenzoylguanidine hydrochloride, m.p.: 193° C.;

EXAMPLE 33

3-N,N-Di-1'-butylsulfamoyl-4-piperidinobenzoylguanidine hydrochloride, m.p.: 212°–214° C.;

EXAMPLE 34

4-Cyclohexylsulfinyl-3-methylsulfonylbenzoylguanidine hydrochloride, m.p.: 222° C.;

EXAMPLE 35

4-(1-Butylthio)-3-methylsulfonylbenzoylguanidine hydrochloride, m.p.: 205° C.;

EXAMPLE 36

4-(2-Chlorophenylthio)-3-methylsulfonylbenzoylguanidine hydrochloride, m.p.: 260° C.;

EXAMPLE 37

4-Phenoxy-3-methylsulfonylbenzoylguanidine hydrochloride, m.p.: 300° C.;

Preparation of 4-phenoxy-3-methylsulfonylbenzoic acid (starting material, m.p. 183°–185° C.) by reaction of methyl 4-chloro-3-methylsulfonylbenzoate with potassium phenoxide in boiling N,N-dimethylacetamide for 16 hours, removal of the solvent by distillation, dissolution in water and acidification with aqueous HCl to pH 1.

Further reaction according to procedure I for the title compound.

EXAMPLE 38

4-(3,5-cis-Dimethyl-1-piperidino)-3-methylsulfonylbenzoylguanidine, m.p.: 219°–220° C.;

EXAMPLE 39

4-Heptamethylenimino-3-methylsulfonylbenzoylguanidine hydrochloride, m.p.: 204° C.;

EXAMPLE 40

4-(4-Methoxyphenylamino)-3-methylsulfonylbenzoylguanidine hydrochloride, m.p.: 222° C.;

EXAMPLE 41

4-(3-Methylphenylamino)-3-methylsulfonylbenzoylguanidine hydrochloride, m.p.: 255°–260° C.;

EXAMPLE 42

4-(2,4-Dimethylphenylamino)-3-methylsulfonylbenzoylguanidine hydrochloride, m.p.: 296°14 297 C.;

EXAMPLE 43

4(1-Butylsulfinyl)-3-methylsulfonylbenzoylguanidine hydrochloride, m.p.: 202° C.;

EXAMPLE 44

4-Methoxy-3-methylsulfonylbenzoylguanidine hydrochloride, m.p.: 253° C.;

EXAMPLE 45

4-(2-Methyl-1-propyloxy) 3-methylsulfonylbenzoylguanidine hydrochloride, m.p.: 164°–166° C.;

EXAMPLE 46

4-(1-Butylsulfonyl)-3-methylsulfonylbenzoylguanidine hydrochloride, m.p.: 217° C.;

EXAMPLE 47

4-Cyclohexylsulfonyl-3-methylsulfonylbenzoylguanidine hydrochloride, m.p.: 292° C.;

EXAMPLE 48

4-(2-Methoxyphenylthio)-3-methylsulfonylbenzoylguanidine hydrochloride, m.p.: 181° C.;

EXAMPLE 49

4-(2-Methylphenylthio)-3-methylsulfonylbenzoylguanidine hydrochloride, m.p.: 312° C.;

EXAMPLE 50

4-Benzyloxy-3-methylsulfonylbenzoylguanidine hydrochloride, m.p.: 236° C.;

EXAMPLE 51

4-(3-Chlorophenylamino)-3-methylsulfonylbenzoylguanidine hydrochloride, m.p.: 294° C.;

EXAMPLE 52

4-(2,4-Dichlorobenzylamino)-3-methylsulfonylbenzoylguanidine hydrochloride, m.p.: 192° C.;

EXAMPLE 53

4-(2,4-Dimethylphenylthio)-3-methylsulfonylbenzoylguanidine hydrochloride, m.p.: 273° C.;

EXAMPLE 54

4-(2,6-Dichlorophenylthio)-3-methylsulfonylbenzoylguanidine hydrochloride, m.p.: 258° C.;

EXAMPLE 55

4-(3-Chlorophenylthio)-3-methylsulfonylbenzoylguanidine hydrochloride, m.p.: 267° C.;

EXAMPLE 56

4-(2,5-Dichlorophenylthio)-3-methylsulfonylbenzoylguanidine hydrochloride, m.p.: 226° C.;

EXAMPLE 57

3-Methylsulfonylbenzoylguanidine hydrochloride, 263°–267° C.;

EXAMPLE 58

4-(4-Chlorobenzylamino)-3-methylsulfonylbenzoylguanidine hydrochloride, m.p.: 230° C.;

The following salts are obtained by reaction of 3-methylsulfonyl-4-piperidinobenzoylguanidine with an appropriate acid:

EXAMPLE 59

3-Methylsulfonyl-4-piperidinobenzoylguanidinium citrate, dec. point 185° C.

EXAMPLE 60

3-Methylsulfonyl-4-piperidinobenzoylguanidinium tartrate, m.p. 140° C.;

EXAMPLE 61

3-Methylsulfonyl-4-piperidinobenzoylguanidinium ethanesulfonate, m.p. 218° C.;

EXAMPLE 62

3-Methylsulfonyl-4-piperidinobenzoylguanidinium fumarate, m.p. 242° C.;

EXAMPLE 63

3-Methylsulfonyl-4-piperidinobenzoylguanidinium glucuronate, m.p. 190° C.;

EXAMPLE 64

3-Methylsulfonyl-4-piperidinobenzoylguanidinium sulfate, m.p. 110° C.;

EXAMPLE 65

3-Methylsulfonyl-4-piperidinobenzoylguanidinium malonate, m.p. 180° C.;

EXAMPLE 66

3-Methylsulfonyl-4-piperidinobenzoylguanidinium gluconate, m.p.: amorphous substance, no defined melting point.

EXAMPLE 67

3-Methylsulfonyl-4-piperidinobenzoylguanidinium lactate, m.p. 125° C.;

EXAMPLE 68

3-Methylsulfonyl-4-piperidinobenzoylguanidinium methanesulfonate; m.p. 255° C.;

EXAMPLE 69

3-Methylsulfonyl-4-piperidinobenzoylguanidinium-4-toluenesulfonate, m.p. 220° C.;

EXAMPLE 70

3-Methylsulfonyl-4-piperidinobenzoylguanidinium tartron acid salt, m.p. 206° C.

EXAMPLE 71

3-Methylsulfonyl-4-(2,6-cis-dimethylpiperidino)benzoylguanidine methanesulfonate, m.p. 203° C. Preparation of 3-methylsulfonyl-4-(2,6-cis-dimethylpiperidino)benzoic acid (starting material as in procedure 1; viscous amorphous product) by boiling 4-fluoro-3-methylsulfonylbenzoic acid in excess 2,6-cis-dimethylpiperidine for 24 hours, removing the solvent by distillation and then acidifying to pH 1 using hydrochloric acid.

EXAMPLE 72

4-(4-Chlorophenoxy)-3-sulfamoylbenzoylguanidine hydrochloride, m.p. 305° C.

EXAMPLE 73

4-tert-Butyl-3-methylsulfonylbenzoylguanidine hydrochloride, amorph.

EXAMPLE 74

4-(1-Methylpropyl)-3-methylsulfonylbenzoylguanidine hydrochloride, m.p. 228°–230° C.
Synthesis route:
a)
Methyl 4-(1-methylpropyl)-3-methylsulfonylbenzoate is obtained from methyl 4-bromo-3-methylsulfonylbenzoate by cross-coupling with 1.5 equivalents of isobutylzinc chloride (from sec-butylmagnesium chloride by transmetallation with zinc(II) chloride etherate in THF) by stirring at room temperature in the presence of catalytic amounts of palladium(II)[1,1'-bis-(diphenylphosphino)ferrocene] chloride and copper(I) iodide, aqueous workup, extraction with ethyl actate and subsequent column chromatography on silica gel using ethyl acetate/nheptane (3:7), colorless oil.
b)
4-(1-Methylpropyl)-3-methylsulfonylbenzoylguanidine hydrochloride from a) by boiling in THF in the presence of guanidine analogously to general procedure II and subsequent treatment with HCl to form the hydrochloride.

EXAMPLE 75

4-Butyl-3-methylsulfonylbenzoylguanidine hydrochloride, m.p. 213°–215° C.

EXAMPLE 76

4-(2-methylpropyl)-3-methylsulfonylbenzoylguanidine hydrochloride, m.p. 229°230° C.
Synthesis route:
a)
Methyl 4-(2-methylpropyl)-3-methylsulfonylbenzoate is obtained from methyl 4-bromo-3-methylsulfonylbenzoate by cross-coupling with 1.5 equivalents of isobutylzinc chloride (from isobutylmagnesium chloride by transmetallation with zinc(II) chloride etherate in THF) by stirring at room temperature in the presence of catalytic amounts of palladium (II) [1,1'-bis-(diphenylphosphino)ferrocene] chloride and copper(I) iodide, aqueous workup, extraction with ethyl actate and subsequent column chromatography on silica gel using ethyl acetate/n-heptane (3:7), colorless oil.
(b)
4-(2-Methylpropyl)-3-methylsulfonylbenzoylguanidine hydrochloride from a) by boiling in THF in the presence of guanidine analogously to general procedure II and subsequent treatment with HCl to form the hydrochloride.

EXAMPLE 77

4-(4-Hydroxyphenoxy)-3-methylsulfonylbenzoylguanidine hydrochloride, m.p. 258°–259° C.; Preparation by catalytic hydrogenation of 4-(4-benzyloxy-phenoxy)-3-methylsulfonylbenzoylguanidine hydrochloride (Example 78) using Pd/C catalyst in glacial acetic acid at room temperature and 760 mm pressure.

EXAMPLE 78

4-(4-Benzyloxyphenoxy)-3-methylsulfonylbenzoylguanidine hydrochloride, m.p. 282° C.

Preparation

Step 1: 4-(4-Benzyloxyphenoxy)-3-methylsulfonylbenzoic acid (m.p. 166≧169° C.):
Reaction of methyl 4-chloro-3-methylsulfonylbenzoate with 4-benzyloxyphenol in dimethylformamide in the presence of $K_2CO_3$ at 80° C. for 10 hours, removal of the solvent by distillation and alkaline hydrolysis of the methyl 4-(4-benzyloxyphenoxy)-3-methylsulfonylbenzoate thus obtained using NaOH in water.

Step 2 to give title compound of Example 78: Reaction of step 1 analogously to general procedure I.

EXAMPLE 79

4-Benzyloxy-3-methylsulfonylbenzoylguanidine, m.p.217° C.

EXAMPLE 80

4-Hydroxy-3-methylsulfonylbenzoylguanidine, m.p. 280° C. (decomposition), is prepared by catalytic hydrogenation of Example 79 using Pd/C catalyst in acetic acid.

We claim:
1. A compound selected from the group consisting of:
4-N,N-diethylamino-3-methylsulfonylbenzoylguanidine hydrochloride,
4-(4-chlorophenoxy)-3-methylsulfonylbenzoylguanidine hydrochloride,
4-(4-fluorophenoxy)-3-methylsulfonylbenzoylguanidine hydrochloride,
4-(4-fluoroanilino)-3-methylsulfonylbenzoylguanidine hydrochloride,
4-(3-chloro-4-fluoro-anilino)-3-methylsulfonylbenzoylguanidine hydrochloride,
4-isopropyl-3-methylsulfonylbenzoylguanidine hydrochloride,
4-isopropyl-3-methylsulfonylbenzoylguanidine methanesulfonate,
3-methylsulfonyl-4-(2,6-cis-dimethylpiperidino)benzoylguanidine methanesulfonate,
4-(1-methylpropyl)-3-methylsulfonylbenzoylguanidine hydrochloride,
4-(2-methylpropyl)-3-methylsulfonylbenzoylguanidine hydrochloride, or a pharmacologically tolerable salt of any of said compounds.
2. A compound selected from the group consisting of:
4-isopropyl-3-methylsulfonylbenzoylguanidine methanesulfonate,
4-isopropyl-3-methylsulfonylbenzoylguanidine hydrochloride,
4-(4-chlorophenoxy)-3-methylsulfonylbenzoylguanidine hydrochloride or a pharmacologically tolerable salt of any of said compounds.
3. The compound 4-isopropyl-3-methylsulfonylbenzoylguanidine methanesulfonate.
4. A pharmaceutical composition for the treatment of arrhythmias comprising an effective amount of a compound as claimed in claim 1, together with at least one pharmaceutical auxiliary.
5. A method for treating arrhythmias, which comprises administering to a host an effective amount of a compound as claimed in claim 1.

* * * * *